(12) United States Patent
Taylor et al.

(10) Patent No.: US 7,858,087 B2
(45) Date of Patent: *Dec. 28, 2010

(54) ENHANCING THE EFFICACY OF IMMUNOTHERAPIES BY SUPPLEMENTING WITH COMPLEMENT

(75) Inventors: Ronald P. Taylor, Charlottesville, VA (US); Margaret A. Lindorfer, Charlottesville, VA (US); Michael D. Solga, Charlottesville, VA (US); Adam Kennedy, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 657 days.

This patent is subject to a terminal disclaimer.

(21) Appl. No.: 11/881,036

(22) Filed: Jul. 25, 2007

(65) Prior Publication Data

US 2007/0298044 A1    Dec. 27, 2007

Related U.S. Application Data

(63) Continuation of application No. 10/486,438, filed as application No. PCT/US02/25273 on Aug. 9, 2002, now Pat. No. 7,255,858.

(60) Provisional application No. 60/311,451, filed on Aug. 10, 2001, provisional application No. 60/318,295, filed on Sep. 10, 2001, provisional application No. 60/374,336, filed on Apr. 22, 2002, provisional application No. 60/373,785, filed on Apr. 19, 2002.

(51) Int. Cl.
*A61K 39/395* (2006.01)
*A61K 35/16* (2006.01)
*C12P 21/08* (2006.01)
*C07K 16/28* (2006.01)
*C07K 19/00* (2006.01)

(52) U.S. Cl. .............. 424/133.1; 424/141.1; 424/142.1; 424/143.1; 424/530; 424/531; 530/387.3; 530/388.1; 530/388.15; 530/388.22; 530/380

(58) Field of Classification Search ..................... None
See application file for complete search history.

(56) References Cited

U.S. PATENT DOCUMENTS

| | | | | |
|---|---|---|---|---|
| 5,736,137 | A * | 4/1998 | Anderson et al. | 424/133.1 |
| 6,455,043 | B1 * | 9/2002 | Grillo-Lopez | 424/155.1 |
| 6,572,856 | B1 * | 6/2003 | Taylor et al. | 424/130.1 |

OTHER PUBLICATIONS

Van der Kolk et al, British J Haematology 115: 807-811, 2001.*
Golay et al, Blood 95(12): 3900-3908, 2000.*
Harjunpaa, A. et al., Scand. J. Immunol. 51:634-641 (2000).
Gilleece, M.H. et al., Blood, 82(3):807-812 (1993).
Reff, M.E. et al., "Depletion of B Cells in Vivo by a Chimeric Mouse Human Monoclonal Antibody to CD20," Blood, vol. 83, No. 2, 1994, pp. 435-445.
Van Der Kolk, L.E. et al., "Complement activation plays a key role in the side-effects of rituximab treatment," British Journal of Haematology, 115, 2001, pp. 807-811.

* cited by examiner

*Primary Examiner*—Phuong Huynh
(74) *Attorney, Agent, or Firm*—Barnes & Thornburg, LLP

(57) ABSTRACT

The present invention is directed to a composition and method for enhancing the complement-mediated cytotoxicity of therapeutic antibodies for their target cells (i.e. those cells displaying the target epitope). More particularly the present invention enhances the efficacy of such therapies by providing a supplemental source of complement.

7 Claims, 2 Drawing Sheets

ENHANCING THE EFFICACY OF IMMUNOTHERAPIES BY SUPPLEMENTING WITH COMPLEMENT

RELATED APPLICATIONS

This application is a continuation of U.S. application Ser. No. 10/486,438, filed on Feb. 9, 2004 U.S. Pat. No. 7,255,858, a national stage of PCT/US2002/025273, filed Aug. 9, 2002, which claims priority under 35 USC §199(e) to U.S. Provisional Application Ser. Nos. 60/311,451, filed Aug. 10, 2001, 60/318,295, filed Sep. 10, 2001, 60/373,785, filed Apr. 19, 2002 and 60/374,336, filed Apr. 22, 2002, the disclosures of which are incorporated herein.

FIELD OF THE INVENTION

The present invention is directed to novel therapeutic compositions and an improved method of treating illness through immunotherapy. The improvement relates to providing a supplemental source of complement to enhance the cytotoxic activity of therapeutic antibodies for those cells that display the target epitope.

BACKGROUND OF THE INVENTION

There is a voluminous literature which describes the use of mAbs in the treatment of cancer, including antibodies against B-cell malignancies as described in U.S. Pat. Nos. 4,987,084 and 6,183,744, the disclosures of which are incorporated herein. These anti-cancer mAbs function by binding specifically to a tumor or circulating cancer cell, and after binding the mAb, killing the cancer cell by one or more mechanisms. These mechanisms can include complement-mediated cytotoxicity (CMC) or opsonization; antibody-dependent cell mediated cytotoxicity (ADCC); induction of programmed cell death (Apoptosis); interference with a particular cell function by blocking a receptor or upregulating/downregulating a particular signaling process. Many mAb based therapies have failed because the mAbs did not facilitate one or more of these functions efficiently.

With respect to complement activation, it is now well-recognized that one of the mechanisms by which cancer cells evade complement-mediated lysis or opsonization is by upregulating normal complement control proteins. In particular, CD46, CD55, and CD59 may be expressed at increased levels on cancer cells (compared to normal cells) and thus they are not killed by complement activation. However, there is yet another reason why a mAb may not be able to induce ADCC or opsonization of a tumor or cancer cell. Quite often complement levels are substantially reduced in cancer patients due to their disease. More particularly, one or more components of the complement cascade may be sufficiently reduced so that the mechanisms by which the mAb uses complement to facilitate cell killing (opsonization or direct lysis (CMC)) may not work effectively.

Currently there are several monoclonal antibodies (mAbs) that are being used to treat cancer including RITUXIMAB (Idec, chimeric), B1(Coulter mouse IgG2a), PANOREX (Glaxo IgG2a), C225 (Imclone chimeric IgG), VITAXIN (Medimmune chimeric IgG), Smart M195 and 1D10 (PDL humanized IgG mAbs) and CAMPATH (Berlex humanized IgG1). In particular, one of these mAbs, RITUXIMAB, has been FDA-approved for the treatment of Non-Hodgkin's Lymphoma. The mechanism used by these antibodies to effect cancer cell death is currently subject to debate. Specifically, a number of investigators contend that RITUXIMAB kills via non-complement mechanisms including Apoptosis, and Fc receptor mediated phagocytosis. However, the present invention is based in part on applicants' belief that both mAbs RITUXIMAB and CAMPATH mediate cell killing predominantly through complement activation. Since the role of complement in the mechanism of action of RITUXIMAB is still being debated, the importance of measuring complement and supplementing its levels in patients being administered therapeutic antibodies has not been previously considered. Applicants' own work (see Example 1) strongly suggests that the only important mechanism by which RITUXIMAB mediates killing of cancer cells is through complement.

It has been reported that treatment of patients with RITUXIMAB for Non-Hodgkin's Lymphoma and other B Cell lymphomas typically gives a response rate of 50%. Experiments conducted in applicants' laboratory-indicate that the active form of RITUXIMAB (RTX) in vivo is RTX covalently associated with C3b(i). It is believed that C3b(i) bound to RTX or other therapeutic mAbs provides a platform targeting epitope. If RITUXIMAB's mechanism of action requires robust complement activation, then the reduced levels of complement proteins that are often observed in cancer patients may be the cause of many of the patients' failure to respond to RITUXIMAB therapy. Furthermore, even if a patient initially has an adequate supply of complement, if that patient's tumor burden is substantial, treating with large amounts of a mAb whose mechanism of action requires complement activation may result in the available complement being used up or substantially depleted. Moreover, megadosing with additional mAb will not resolve the underlying problem relating to the lack of available complement and will not increase the effectiveness of the treatment.

The effectiveness of RTX, and other therapeutic mAbs, can be enhanced, however, if complement is restored with fresh plasma, or with individual components of the complement system (either purified natural components or recombinantly produced complement components). The improvement relates to identifying patients that will be refractory for anti-cancer passive immunotherapy due to inadequate levels of complement activity, and enhancing the efficacy of such therapy by providing a supplemental source of complement proteins.

SUMMARY OF THE INVENTION

The present invention is directed to compositions and methods for enhancing the complement-mediated cytotoxic efficacy of antibody based anti-tumor therapies. In particular, the present invention is directed to enhancing the efficacy of RITUXIMAB and other anti-tumor mAb treatments by providing patients with a supplemental source of complement, either as fresh plasma/sera or as isolated complement components. The following abbreviations are used throughout the application and have the following meanings: C=complement; RTX=RITUXIMAB; NHS=Normal Human Serum (a normal complement source); CP=citrated human plasma (also a complement source).

DETAILED DESCRIPTION OF THE INVENTION

Definitions

Figure 1A:
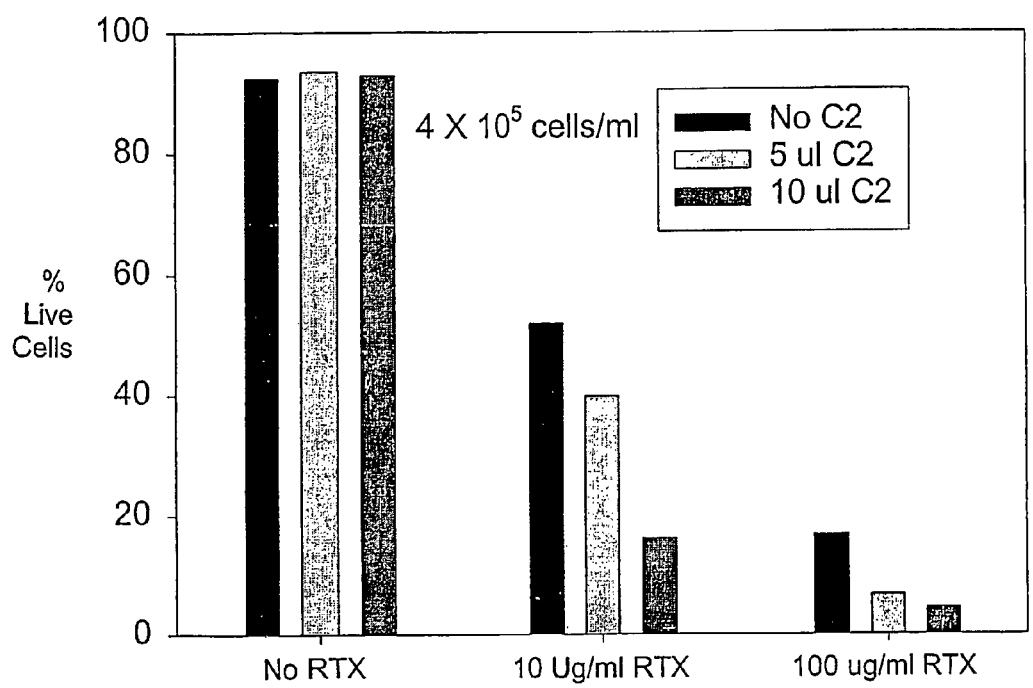
FIGS. 1A & 1B are bar graphs representing the results of an experiment in which flow cytometry was used to measure RTX-mediated killing of DB cells over the course of a 24 hour incubation. At cell concentrations of $3.6 \times 10^6$, use of 100 ug/ml RTX leaves more than half of the cells alive after 24 hours. Supplementation of the serum with C2 leads to a substantial increase in killing, as illustrated in the large drop in live cells in the presence of both RTX and C2. Note that C2 by itself in serum does not promote killing.

In describing and claiming the invention, the following terminology will be used in accordance with the definitions set forth below.

The following abbreviations are used throughout the application and have the following meanings: C=complement; RTX=RITUXIMAB; NHS=Normal Human Serum (a normal complement source); CP=citrated human plasma (also a complement source).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is $C_1$-$C_4$ alkyl;

2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or $C_1$-$C_4$ alkyl with the proviso that R and R$_1$ are not both hydrogen;

3. peptides wherein the C terminus is derivatized to —C(O)R$_2$ where R$_2$ is selected from the group consisting of $C_1$-$C_4$ alkoxy, and —NR$_3$R$_4$ where R$_3$ and R$_4$ are independently selected from the group consisting of hydrogen and $C_1$-$C_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Vat or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

As used herein, the term "purified" and like terms relate to the isolation of a molecule or compound in a form that is substantially free (i.e. at least 60% free, preferably 80% free, and most preferably greater than 90% free) from other components with which they are naturally associated.

As used herein, the term "treating" includes alleviating the symptoms associated with a specific disorder or condition and/or preventing or eliminating said symptoms. For example, treating cancer includes preventing or slowing the growth and/or division of cancer cells as well as killing cancer cells.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "parenteral" includes administration intraperitoneally, intraarterially, subcutaneously, intravenously or intramuscularly.

As used herein a "substantially reduction in complement activity" is considered to be any reduction in activity that is greater than 25%.

The Invention

The present invention is based on the observation that antibody based anti-cancer therapies such as RITUXIMAB therapy utilize a mechanism of action that requires complement activation. Quite often complement levels are substantially reduced in cancer patients due to their disease. More particularly, one or more components of the complement cascade may be sufficiently reduced so that the mechanisms by which the mAb uses complement to facilitate cell killing (opsonization or direct lysis (CMC) or killing promoted by complement receptors on effector cells) may not work effectively. Furthermore, even in patients that initially display adequate levels of complement, those levels can be substantially depleted over the course of treatment such that inadequate levels of complement remain during the mid to later stages of treatment. One aspect of the present invention is directed to a method of monitoring the complement capabilities of patients to identify patients that have substantially depleted complement activity. Another embodiment of the invention is directed to a method of enhancing the efficacy of an antibody based therapy by supplementing the treatment with either matched donor plasma or serum (as a source of complement) or purified native or recombinant complement proteins.

If complement activation is required to facilitate a mAb-based therapy, then as a first step, the endogenous level of complement activity in the patient's serum or citrated plasma should be measured. In accordance with one embodiment a method is provided for screening patients to identify individuals that will be refractory to antibody based anti-cancer therapies such as RITUXIMAB therapy. More particularly, one aspect of the present invention is directed to a method of determining a patient's capacity for complement action as an indication of their responsiveness to passive immunotherapy. The method comprises the step of measuring the complement capacity (i.e. the actual levels of complement proteins and complement activity) of the individual. These measurements may include CH50 titrations as well as measurement of the levels of individual complement proteins, to determine if one or more of them are lacking. CH50 assays have been previously described and are well known to those skilled in the art (see Fetterhoff et al., (1984) J. Clin. Lab Immunol 14: 205).

In one embodiment the patient's complement capacity is determined by measuring the ability of the patient's serum/plasma to promote complement-mediated opsonization or killing of cancer cells upon addition of adequate amounts of the anti-cancer antibody. The cancer cells used in such an assay can be isolated from the patient to be treated (e.g. a biopsy sample or isolated from the bloodstream) or taken from established cell lines that serve as model systems for the particular cancer type afflicting the patient. Opsonization includes deposition of activated fragments of component proteins C3 and/or C4 on the cancer cells. Alternatively, the patient's complement capacity may be determined by measuring the patient's CH50. Those individuals that have substantially reduced complement capacity will be refractory for antibody based therapies that require robust complement activity, such as RITUXIMAB therapy.

In one embodiment, the measurement of a patient's complement capacity is made using the patient's serum or citrated plasma (both are acceptable complement sources) and compared to the measurement obtained using compatible donor-matched serum or citrated plasma that is known to have a normal and robust level of complement activity. If the patient's complement levels are deemed adequate, then the mAb based therapy can be initiated. However, the complement capacity of the patient still needs to be monitored throughout the treatment to ensure adequate levels of complement are maintained during the entire treatment.

One aspect of the present invention relates to a method of improving the effectiveness of antibody mediated anti-cancer therapies. The method comprises the step of measuring complement levels in a patient prior to administering a dose of the therapeutic anti-neoplastic antibody. The actual levels of complement proteins and complement activities are often reduced in patients suffering from a variety of different cancers. In addition, the patient's ability to replace complement proteins may be impaired or the tumor burden may be so great that sufficient complement is not present for the entire treatment. When a patient's capacity for complement activation is low, as determined for example, by a low CH50 level, then the administration of the anti-cancer antibody therapy can be supplemented with fresh plasma/serum from a compatible donor or with purified components from the complement cascade. Typical CH50 levels in healthy individuals with functional complement will range from about 100 to about 300. Any individual that has a CH50 level of 150 or lower will likely receive benefit from administration of exogenous, supplemental complement proteins.

Alternatively, measurements of complement activity, as defined by assays that combine an anti-cancer antibody (such as RITUXIMAB), cancer cells and the patient's serum/plasma, may be required to identity individuals likely to benefit from treatment. Reduction of efficacy by a factor of two or more in either opsonization or cell killing will provide an approximate standard for such identification. Furthermore, the assay can be extended to confirm, or identify, those patients that would benefit from supplementing immunotherapy with a source of complement proteins. The assay comprises obtaining a serum or plasma sample from the patient and measuring the ability of the patient's serum/plasma to promote complement-mediated opsonization or killing of cancer cells upon addition of adequate amounts of the anti-cancer antibody in the presence and absence of complement. When significant additional opsonization or killing of cancer cells occurs in the presence of supplemental complement, then administration of supplemental complement in conjunction with the anti-cancer antibody therapy is warranted. The cancer cells used in such an assay can be isolated from the patient to be treated (e.g. a biopsy sample or isolated from the bloodstream) or taken from established cells lines that serve as model systems for the particular cancer type afflicting the patient. Opsonization includes deposition of activated fragments of component proteins C3 and/or C4 on the cancer cells.

In accordance with one embodiment a method of identifying individuals who would benefit from complement supplementation of an anti-cancer immunotherapy is provided. The method comprises the steps of obtaining a serum or plasma sample from the patient to be treated and contacting the serum or plasma sample with cancer cells and the anti-cancer antibody to form a reaction mixture. The reaction mixture is then incubated for a predetermined length of time in the presence and absence of donor complement proteins. A determination is then made of whether the serum or plasma sample exhibits higher opsonization or cell killing in the presence of the supplemental donor complement proteins. Those patients whose serum/plasma give a higher level of opsonization or cell killing in the presence of supplement complement are thus identified as individuals whose anti-cancer antibody therapy would benefit from complement supplementation.

In this method, the serum or plasma sample is typically isolated from the patient, combined with the relevant cancer cells (i.e. cancer cells isolated from the patient or an established cell line that serves as a model for the patient's cancer) and the therapeutic anti-cancer antibody, and then divided into two separate reaction mixtures. Supplemental donor complement proteins are then added to the first reaction mixture and not the second reaction mixture. Enhanced opsonization or cell killing that occurs in the first reaction mixture relative to the second reaction mixture indicates that supplementation with donor complement would be beneficial in enhancing the in vivo efficacy of the anti-cancer immunotherapy.

Donor serum or citrated plasma is used in one embodiment to provide a source of complement, however individual complement components can also be used to supplement patient complement activity. In accordance with one embodiment an improved composition is provided for treating cancer patients with an antibody based anti-cancer therapy, wherein the patient exhibits substantially lower levels of complement activity before or during the treatment. A detected substantial reduction in complement activity (i.e. greater than 25%) resulting from antibody based anti-cancer therapy will lead to complement supplementation in accordance with the present invention. More particularly, cancer patients having CH50 levels, at any time, of less than 150, or more preferably less than 100, would benefit from the administration of the improved immunotherapy compositions of the present invention. The improved composition comprises an anti-neoplastic antibody and a composition comprising a complement protein. In accordance with one embodiment the complement protein is provided as a fresh serum or fresh citrated plasma isolated from a compatible donor. In one embodiment the serum/plasma is prepared from individuals having AB blood type.

The amount of donor serum or plasma that will be administered to an individual will be varied base on the severity of complement deficiency in the patient. However, typically the patient will be administered about one to two units of plasma or serum. The donor serum/plasma can be administered separately or as an admixture with anti-cancer antibody.

In addition to, or as an alternative to, using serum or plasma to supplement patient complement function during anti-cancer immunotherapy (or other antibody-based therapy that relies on complement fixation for its mechanism of action), individual purified complement proteins/factors can be used. The purified complement proteins/factors can be isolated from natural sources or more preferably the proteins are recombinantly produced and purified. In one embodiment the purified complement proteins/factors are selected from the group consisting of C1-C9, factor B, factor D and properdin and more preferably selected from the group consisting of C1, C2, C3, C4 and C5. In one embodiment the purified complement proteins/factors are selected from the group consisting of C1, C2, and C5. Accordingly, an improved immunotherapy composition is provided wherein the composition comprises one or more anti-tumor antibodies in combination with one or more complement proteins/factors.

Preferably, the complement factors used in conjunction with the anti-cancer antibody therapy will be selected based on their prevalence in the patient to be treated. In particular, it is known that certain components of the complement cascade are more prevalent in humans and other mammals than other components. Since complement protein C2 is typically low relative to the other complement proteins, one aspect of the present invention comprises enhancing the effectiveness of anti-cancer antibody therapy (such as RTX treatment) by supplementation with purified human complement protein C2. In addition it has been reported that the oxidized form of C2 has been shown to be a particularly effective form of that complement protein in facilitating and prolonging complement activation. Accordingly, one embodiment of the present invention encompasses supplementing an antibody therapy (that relies on complement fixation for its mechanism of action) with the administration of oxidized C2.

Preferably the compositions of the present invention further comprises a pharmaceutically acceptable carrier. A pharmaceutical composition comprising one or more individual complement proteins (recombinantly produced or purified natural components, or matched donor serum/plasma) and a pharmaceutically acceptable carrier can be administered separately or as an admixture with the anti-cancer antibody. The composition can be administered to the target cells using any of the known routes including oral, parenteral, transdermal or time release implant. In one preferred embodiment the composition is administered intravenously.

In addition to RTX, other mAbs have been described and are under investigation for the immunotherapy of cancer, including: B1, Coulter mouse IgG2a; Panorex, Glaxo IgG2a; C225, Imclone chimeric IgG; Vitaxin, Medimmune chimeric IgG; Campath, Berlex humanized IgG1; Smart M195 and 1D10, PDL humanized IgG mAbs; OvaRex, AltaRex Corp. murine antibody for ovarian cancer; BEC2, ImClone Systems Inc., murine IgG for treatment of lung cancer; IMC-C225, InClone Systems Inc., chimeric IgG for treatment of head and neck cancer; Vitaxin, MedImmune humanized antibody for treatment of sarcoma; LymphoCide, Immunomedics humanized IgG for treatment of non-Hodgkin's lymphoma; Oncolym, Techniclone, Inc., murine antibody for treatment of non-Hodgkin's lymphoma; use of the anti-C3b(i) mAb 3E7 (or the next generation mAb) in a radioactive form: 131-I, or 90-Y; as well as Alemtuzumab; Ibritumomab; Gemtuzumab; Epratuzumab; Apolizumab; HuM195; Trastuzumab; Cetuximab; Edrecolomab; ABX-EGF; 2C4; DM-1; ING-1; Bevacizumab; and Anti-KDR antibodies. Any of these antibodies whose mechanism of action is primarily through complement are candidates for supplementation with complement to enhance the cytotoxic activity of the antibody for its target cells (i.e. those cells displaying an epitope that the antibody specifically binds). Accordingly, it is anticipated that the effectiveness of each of these antibodies could be enhanced if the therapy includes supplementation with an exogenous source of complement (either from matched donor serum/plasma or from supplementation with individual complement proteins).

In accordance with one embodiment of the present invention a method of enhancing the cytotoxic activity of anti-neoplastic antibodies for their target cells is provided. The method comprises the steps of contacting the target cells with one or more anti-neoplastic antibodies and contacting the target cells with a composition comprising donor human complement proteins. The target cells can be contacted either in vitro or in vivo with the anti-neoplastic antibodies and the donor complement proteins, in any particular order or the two can be administered simultaneously. In one preferred embodiment the target cells are first contacted with the donor complement and then the anti-neoplastic antibody is added for contact with the target cells. When the target cells are contacted in vivo the compositions comprising the anti-neoplastic antibody and the complement are typically administered intravenously, although other parenteral routes of administration are also possible.

In one embodiment the donor complement composition comprises fresh serum or citrated plasma, prepared from a human donor having a matched blood type and optionally supplemented with purified recombinantly produced complement proteins such as C2. In one embodiment the human donor for the plasma/serum has AB blood type. Alternatively, the donor complement composition comprises one or more purified members of the complement cascade, including proteins produced using recombinant technologies. In one preferred embodiment the composition comprises complement protein C2, in particular, oxidized C2.

In one embodiment a method is provided for treating a B-cell malignancy. The method comprises administering to a human subject having a B-cell malignancy a therapeutic composition comprising a pharmaceutically acceptable carrier and an anticancer antibody specific for B-cells as well as a composition comprising a source of complement factors. The two compositions can be administered simultaneously or separately and in one embodiment the two are combined to form a single composition comprising an anticancer antibody specific for B-cells, a source of complement factors and a pharmaceutically acceptable carrier. In one embodiment the composition is administered parenterally (preferably intravenously) either continuously or in multiple doses. In one embodiment the anticancer antibody component comprises at least two monoclonal antibodies that bind with distinct epitopes uniquely expressed on cancer cells. This method can be used to treat various B-cell malignancies including indolent forms of B-cell lymphomas, aggressive forms of B-cell lymphomas, chronic lymphocytic leukemias, and acute lymphocytic leukemias, and in one embodiment the method is used to treat non-Hodgkin's lymphoma. The therapeutic composition can further include additional anticancer agents that are known to those skilled in the art, including cytokines and chemotherapeutic agents.

The method of enhancing an antibody's effectiveness in killing its target cells by supplementing with exogenous complement can be used with any mAb-based therapy whose action is believed to require complement activation. Such therapies can include cancer as well as other diseases including infectious disease or conditions in which certain cells are targeted to increase or decrease a particular biological activity. The patient can be monitored before and during the course of treatment with a therapeutic antibody. When the patient's complement drops below a certain threshold (for example a CH50 of less than 120), then the patient is administered an intravenous infusion with compatible serum/plasma from a normal individual with sufficiently high levels of complement activity (or an effective amount of one or more recombinantly produced complement proteins) either before or simultaneously with subsequent doses of the therapeutic antibody.

Accordingly, the present invention is also directed to the use of supplemental complement (comprising either donor serum/plasma or individual complement proteins such as C2)

to enhance the effectiveness of antibody therapy for any antibody-based treatment that involves a disease wherein complement is low. For example, diseases other than cancer that often have low complement titers include diseases that are characterized by inflammation, such as infectious disease, autoimmune disorders (e.g. lupus erythematosus and rheumatoid arthritis) or conditions in which certain cells are targeted for destruction or removal as a means to increase or decrease a particular biological activity. Autoimmune diseases can be treated with anti-B cell antibodies, such as RITUXIMAB and such treatments can be supplemented with complement factors in accordance with the present invention through the administration of normal compatible donor plasma.

Accordingly, the method of supplementing with complement can be used as a general strategy for enhancing the efficacy of an antibody-based therapy whose action is believed to require complement activation, and where the afflicted individual has a lowered capacity for complement activation. The method comprises the steps of administering complement factors that are low or missing from the individual in conjunction with the administration of the mAb-based therapy. The supplemental complement factors can be administered either before or after the administration of the mAb-based therapy or simultaneously with the therapeutic antibodies. In one preferred embodiment the supplemental complement factors are combined with the therapeutic antibodies and administered as a single composition.

The present invention also encompasses a pack or kit comprising a source of complement for use with immunotherapy applications. In accordance with one embodiment a kit for enhancing the cytotoxic activity of anti-tumor antibodies is provided wherein the kit comprises human serum or plasma (isolated from either an AB blood type donor or a matched blood type donor) or one or more purified complement proteins. The purified complement is preferably a recombinant produced protein selected from the group consisting of C1, C2, C3, C4, C5, C6, C7, C8, C9, factor B, factor D and properdin. The genes encoding human complement proteins have been cloned and any reference herein to "recombinant complement proteins" is intended to cover recombinantly produced complement proteins that have the natural amino acid sequence as well as proteins whose amino acid sequence has been modified (by amino acid deletions, additions or substitutions or by other modifications) but still retain the native complement protein's function. For example, the amino acid sequence of a complement protein may be modified to enhance its functional half life in vivo or enhance its shelf life. In one embodiment the recombinant protein is selected from the group consisting of C2, C3 and C4, with C2, and more particularly, oxidized C2 being the most preferred complement protein. In one embodiment the kit further comprises a therapeutic antibody such as an anti-cancer antibody, including anti-cancer antibodies selected from the group consisting of RITUXIMAB and CAMPATH.

The kits of the present invention may further comprise reagents for detecting and monitoring complement function in an individual. More particularly the kit may include reagents for determining CH50 levels and/or reagents for monitoring the opsonization of the target cells. Accordingly, the kit may include antibodies that are directed against C3b (i), such as mAb 3E7 or 7C12. These antibodies may be derivatized with fluorescein or other fluorescent signaling moieties. The complement proteins and the therapeutic and diagnostic antibodies of the kit can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

Example 1

RITUXIMAB Mediates Cell Killing Through Complement Activation

To determine if complement activation is correlated with RTX binding to cells, two CD20-positive cell lines were reacted with RTX in a variety of sera. The readout for complement activation in these experiments is the covalent deposition of activated fragments of complement protein C3 (defined herein as C3b(i)) on the cells. Mab 3E7, which binds to activated C3b(i) bound to cells, was also used in these experiments to enhance RTX-mediated complement activation. Direct and indirect RIA was used to quantitate deposition of C3b(i) and binding of nab 3E7 to Raji or ARH-77 cells when a variety of NHS were used for C opsonization. Radiolabeled nab 7C12, which binds to C3b(i), was used for the primary readout.

The results in 50% NHS, summarized in Table 1, indicate that in the presence of both RTX and mAb 3E7, >1 million molecules of C3b(i) bind per Raji cell, and reduced but still substantial C opsonization occurs in the presence of either one of the mAbs alone. Binding of RTX alone, in NHS, to both cell lines led to significant increases in C3b(i) opsonization. In the presence of RTX, mAb 3E7 appears to facilitate a chain reaction in which binding of C3b(i) to the cells leads to binding of mAb 3E7, which may either modestly activate C (mAb 3E7 is murine isotype IgG1) and/or enhance capture of additional molecules of C3b(i). RIA with $^{125}$I-RTX revealed that 220,000±43,000 molecules (n=7) bound to Raji cells, and 310,000±60,000 molecules (n=4) bound to ARH-77 cells, in the presence and absence of C. Approximately 1,000,000 molecules of mAb 3E7 were found to bind to either of the cells in the presence of RTX and C (Table 1). These experiments thus also demonstrate amplification in the sense that more molecules of C3b(i) are deposited on the cells than bound RTX molecules.

TABLE 1

C3b(i) and mAb 3E7 Bind to CD20+ Cells during C/RTX Opsonization

| | Molecules Bound per Cell[a] | |
|---|---|---|
| | C3b(i)[b] | Anti-C3b(i) mAb 3E7[c] |
| Raji Cells incubated in: | | |
| NHS | 300,000 ± 150,000[d] (18) | NA |
| NHS/RTX | 610,000 ± 190,000 (18) | NA |
| NHS/RTX/ mAb 3E7 | 1,400,000 ± 500,000 (13) | 890,000 ± 220,000 (6) |
| NHS/mAb 3E7 | 680,000 ± 340,000 (14) | 420,000 ± 190,000 (6) |
| ARH-77 Cells incubated in: | | |
| NHS | 150,000 ± 60,000 (10) | NA |
| NHS/RTX | 790,000 ± 230,000 (10) | NA |
| NHS/RTX/ mAb 3E7 | 930,000 ± 240,000 (9) | 1,100,000 ± 200,000 (3) |
| NHS/mAb 3E7 | 370,000 ± 110,000 (9) | 240,000 ± 60,000 (3) |

[a]Average ± S.D. (number of determinations).
[b]Molecules bound were measured by indirect RIA based on probing with $^{125}$I-anti-C3b(i) mAb 7C12.
[c]$^{125}$I-anti-C3b(i) mAb 3E7 was used directly.
[d]Background level of binding of C3b(i) to the Raji (and ARH-77) cells in NHS has been previously reported. Raji cells in NHS activate C, but less C3b(i) is bound than is observed in the presence of RTX.

In summary, for Raji cells, either mAb singly or the combination gave more C3b(i) deposition than NHS alone ($p<10^{-3}$). RTX/mAb 3E7 gave more C3b(i) deposition than either mAb alone ($p<10^{-3}$). More mAb 3E7 was bound in the presence of RTX ($p=3\times10^{-3}$). For ARH-77 cells, either mAb singly or the combination gave more C3b(i) deposition than NHS alone ($p<10^{-3}$). The combination gave more C3b(i) deposition than mAb 3E7 alone ($p<10^{-3}$). More mAb 3E7 was bound in the presence of RTX ($p=2\times10^{-3}$).

Co-Localization of RTX and mAb 3E7.

Fluorescence microscopy was used to address critical questions raised by the RIA experiments concerning the molecular sites of binding of C3b(i) and mAb 3E7 to RTX-opsonized CD20+ cells in the presence of C. When Raji or ARH-77 cells were incubated with red Alexa 594 RTX and green Alexa 488 mAb 3E7 (specific for C3b(i)) together in NHS or citrated plasma, the two mAbs co-localize on the cells, as revealed by coincidence of red and green fluorescence (identified with different microscope filters). In the presence of mAb 3E7 cross-linking of the cells was often observed, as well as capping and/or co-localization of the probes to discrete areas on the cells. If cells are opsonized with red Alexa 594 RTX alone in citrated plasma, washed and then probed with green Alexa 488 mAb 3E7, this green mAb again co-localizes with previously bound red RTX, and in many cases cells are extensively cross-linked. Binding of red RTX alone to cells in the presence or absence of NHS leads to a more homogenous binding pattern and neither capping nor cross-linking is observed.

A negative control experiment reveals that if cells are first reacted with green mAb 3E7 in the presence of NHS and then washed and probed with RTX, the two probes bind to the cells with completely different patterns, and there is no evidence for co-localization. Moreover, the fluorescence pattern of binding of mAb 3E7 to the cells in NHS in the absence of RTX is weal. Similar patterns of complement opsonization and co-localization of mAb 3E7 with RTX were demonstrable in DB cells. In addition, the cross-linking described above was also observed if only one or neither of the two key mAbs (RTX, 3E7) were labeled with fluorescence dyes. These results provide further proof that binding of RTX to CD20 positive cells promotes robust complement activation and C3b(i) deposition.

Finally, to further demonstrate that RITUXIMAB and mAb1F5 mediated cytotoxicity derives from complement activation, flow cytometry was used to monitor the cytotoxic effects of various formulation (see Tables 2-5). Mab1F5 was previously used in a phase I trial for B cell lymphoma, but it has not been commercialized and its mechanism of action has not been defined. Cells were incubated in the presence of media, or sera, ±RITUXIMAB/3E7 etc. The readout is based on flow cytometry, the uptake of propidium iodide indicating cell death, and all experiments were done in duplicate. Gating schemes are used to identify cells. G1 are monodisperse cells, and G4 includes all cells.

TABLES 2A-D

Table 2A

| Raji ($1 \times 10^5$) | 1 Hr G4 Live | 24 Hr G4 Live | 48 Hr G4 Live | 72 Hr G4 Live |
|---|---|---|---|---|
| Media | 10,916 | 20,328 | 61,755 | 79,637 |
|  | 10,075 | 19,791 | 59,396 | 77,878 |
| Media + Ritux | 9,875 | 9,769 | 39,656 | 41,997 |
|  | 8,621 | 10,026 | 34,636 | 39,782 |
| Media ± 1F5 | 8,843 | 12,539 | 40,717 | 46,051 |
|  | 9,741 | 14,218 | 47,101 | 53,389 |

Table 2B

| Raji ($1 \times 10^5$) | 1 Hr G4 Total | 24 Hr G4 Total | 48 Hr G4 Total | 72 Hr G4 Total |
|---|---|---|---|---|
| Media | 12,694 | 23,258 | 65,119 | 85,085 |
|  | 11,791 | 22,608 | 62,722 | 82,337 |
| Media + Ritux | 11,768 | 12,809 | 45,200 | 51,175 |
|  | 10,305 | 12,929 | 39,163 | 47,065 |
| Media + 1F5 | 10,437 | 14,973 | 44,596 | 52,591 |
|  | 11,502 | 17,111 | 51,166 | 59,476 |

Table 2C

| Raji ($1 \times 10^5$) | 1 Hr G1 Live | 24 Hr G1 Live | 48 Hr G1 Live | 72 Hr G1 Live |
|---|---|---|---|---|
| Media | 10,596 | 20,010 | 60,328 | 44,109 |
|  | 9,747 | 19,467 | 58,054 | 41,915 |
| Media + Ritux | 9,513 | 9,371 | 37,416 | 26,511 |
|  | 8,308 | 9,671 | 32,220 | 25,398 |
| Media + 1F5 | 8,541 | 12,377 | 39,065 | 25,428 |
|  | 9,328 | 14,011 | 45,364 | 30,440 |

Table 2D

| Raji ($1 \times 10^5$) | 1 Hr G4 Dead | 24 Hr G4 Dead | 48 Hr G4 Dead | 72 Hr G4 Dead |
|---|---|---|---|---|
| Media | 1,036 | 1,810 | 2,120 | 2,746 |
|  | 979 | 1,727 | 2,033 | 2,240 |
| Media + Ritux | 1,081 | 2,085 | 2,986 | 4,309 |
|  | 956 | 1,977 | 2,469 | 3,285 |
| Media + 1F5 | 928 | 1,640 | 2,278 | 3,293 |
|  | 1,024 | 2,064 | 2,558 | 2,908 |

TABLES 3A-D

Table 3A

| Raji ($1 \times 10^5$) | 1 Hr G4 Live | 24 Hr G4 Live | 48 Hr G4 Live | 72 Hr G4 Live |
|---|---|---|---|---|
| 50% Serum (O+) | 6,201 | 14,783 | 24,956 | 29,536 |
|  | 5,844 | 13,122 | 24,990 | 25,608 |
| 50% Serum (O+) w/ RITUXIMAB | 4,166 | 1,225 | 1,265 | 1,220 |
|  | 3,970 | 915 | 884 | 1,529 |
| 50% Serum (O+) w/ 1F5 | 549 | 695 | 3,632 | 3,677 |
|  | 626 | 611 | 5,016 | 4,776 |
| 50% Serum (O+) w/ RITUXIMAB + mAb 3E7 | 407 | 62 | 109 | 125 |
|  | 400 | 80 | 185 | 85 |
| 50% Serum (O+) w/ 1F5 + mAb 3E7 | 41 | 58 | 312 | 259 |
|  | 39 | 76 | 248 | 385 |

Table 3B

| Raji ($1 \times 10^5$) | 1 Hr G4 Total | 24 Hr G4 Total | 48 Hr G4 Total | 72 Hr G4 Total |
|---|---|---|---|---|
| 50% Serum (O+) | 9,889 | 19,405 | 33,050 | 45,583 |
|  | 8,905 | 17,236 | 32,043 | 40,910 |
| 50% Serum (O+) w/ RITUXIMAB | 9,126 | 12,508 | 10,690 | 11,059 |
|  | 9,244 | 12,302 | 10,560 | 11,816 |
| 50% Serum (O+) w/ 1F5 | 9,732 | 8,608 | 11,991 | 10,124 |
|  | 9,470 | 8,388 | 15,102 | 12,852 |
| 50% Serum (O+) w/ RITUXIMAB + mAb 3E7 | 5,082 | 5,561 | 6,695 | 7,991 |
|  | 4,525 | 5,836 | 10,097 | 7,256 |
| 50% Serum (O+) w/ 1F5 + mAb 3E7 | 8,000 | 5,778 | 7,247 | 6,834 |
|  | 8,418 | 6,844 | 7,915 | 8,537 |

TABLES 3A-D-continued

Table 3C

| Raji (1 × 10⁵) | 1 Hr G1 Live | 24 Hr G1 Live | 48 Hr G1 Live | 72 Hr G1 Live |
|---|---|---|---|---|
| 50% Serum (O+) | 5,979 | 14,287 | 21,807 | 14,597 |
|  | 5,630 | 12,607 | 21,949 | 12,307 |
| 50% Serum (O+) w/ RITUXIMAB | 4,014 | 1,177 | 1,200 | 998 |
|  | 3,814 | 872 | 823 | 1,229 |
| 50% Serum (O+) w/ 1F5 | 490 | 677 | 3,495 | 3,141 |
|  | 545 | 611 | 4,826 | 4,157 |
| 50% Serum (O+) w/ RITUXIMAB + mAb 3E7 | 363 | 42 | 92 | 105 |
|  | 353 | 66 | 155 | 66 |
| 50% Serum (O+) w/ 1F5 + mAb 3E7 | 16 | 39 | 277 | 213 |
|  | 14 | 65 | 219 | 344 |

Table 3D

| Raji (1 × 10⁵) | 1 Hr G4 Dead | 24 Hr G4 Dead | 48 Hr G4 Dead | 72 Hr G4 Dead |
|---|---|---|---|---|
| 50% Serum (O+) | 1,763 | 2,522 | 3,583 | 3,847 |
|  | 1,641 | 2,304 | 2,996 | 3,463 |
| 50% Serum (O+) w/ RITUXIMAB | 3,614 | 11,011 | 9,236 | 9,384 |
|  | 4,053 | 11,095 | 9,529 | 9,734 |
| 50% Serum (O+) w/ 1F5 | 8,680 | 7,503 | 7,483 | 5,494 |
|  | 8,334 | 7,432 | 9,065 | 6,946 |
| 50% Serum (O+) w/ RITUXIMAB + mAb 3E7 | 4,138 | 5,367 | 6,511 | 7,759 |
|  | 3,611 | 5,631 | 9,781 | 7,098 |
| 50% Serum (O+) w/ 1F5 + mAb 3E7 | 7,831 | 5,645 | 6,788 | 6,328 |
|  | 8,225 | 6,689 | 7,915 | 7,789 |

TABLES 4A-D

Table 4A

| Raji (1 × 10⁵) | 1 Hr G4 Live | 24 Hr G4 Live | 48 Hr G4 Live | 72 Hr G4 Live |
|---|---|---|---|---|
| 50% Serum (B+) | 1,054 | 10,833 | 29,740 | 39,145 |
|  | 969 | 10,277 | 26,893 | 36,869 |
| 50% Serum (B+) w/ RITUXIMAB | 3,972 | 1,366 | 530 | 797 |
|  | 4,500 | 1,120 | 941 | 850 |
| 50% Serum (B+) w/ 1F5 | 1,254 | 3,190 | 6,901 | 6,999 |
|  | 717 | 2,046 | 5,196 | 5,561 |
| 50% Serum (B+) w/ RITUXIMAB + mAb 3E7 | 183 | 63 | 114 | 132 |
|  | 143 | 48 | 70 | 77 |
| 50% Serum (B+) w/ 1F5 + mAb3E7 | 38 | 89 | 706 | 417 |
|  | 23 | 126 | 388 | 436 |

Table 4B

| Raji (1 × 10⁵) | 1 Hr G4 Total | 24 Hr G4 Total | 48 Hr G4 Total | 72 Hr G4 Total |
|---|---|---|---|---|
| 50% Serum (B+) | 9,744 | 17,916 | 26,000 | 47,812 |
|  | 9,028 | 17,031 | 24,000 | 45,643 |
| 50% Serum (B+) w/ RITUXIMAB | 9,182 | 11,800 | 10,064 | 10,481 |
|  | 10,650 | 13,268 | 13,875 | 11,542 |
| 50% Serum (B+) w/ 1F5 | 10,814 | 13,036 | 15,239 | 17,451 |
|  | 11,310 | 12,674 | 14,599 | 13,698 |
| 50% Serum (B+) w/ RITUXIMAB + mAb 3E7 | 3,667 | 3,930 | 6,895 | 5,608 |
|  | 2,848 | 3,362 | 4,642 | 6,413 |
| 50% Serum (B+) w/ 1F5 + mAb3E7 | 4,998 | 4,775 | 9,565 | 7,765 |
|  | 6,739 | 5,968 | 7,804 | 8,269 |

TABLES 4A-D-continued

Table 4C

| Raji (1 × 10⁵) | 1 Hr G1 Live | 24 Hr G1 Live | 48 Hr G1 Live | 72 Hr G1 Live |
|---|---|---|---|---|
| 50% Serum (B+) | 996 | 10,488 | 26,286 | 22,614 |
|  | 915 | 9,912 | 24,143 | 21,380 |
| 50% Serum (B+) w/ RITUXIMAB | 3,746 | 1,283 | 499 | 652 |
|  | 4,290 | 1,058 | 873 | 690 |
| 50% Serum (B+) w/ 1F5 | 1,108 | 3,063 | 6,431 | 6,019 |
|  | 624 | 2,046 | 4,913 | 4,580 |
| 50% Serum (B+) w/ RITUXIMAB + mAb 3E7 | 149 | 44 | 108 | 103 |
|  | 118 | 35 | 48 | 62 |
| 50% Serum (B+) w/ 1F5 + mAb3E7 | 16 | 74 | 641 | 357 |
|  | 9 | 104 | 353 | 371 |

Table 4D

| Raji (1 × 10⁵) | 1 Hr G4 Dead | 24 Hr G4 Dead | 48 Hr G4 Dead | 72 Hr G4 Dead |
|---|---|---|---|---|
| 50% Serum (B+) | 4,743 | 5,586 | 5,615 | 5,627 |
|  | 4,501 | 5,274 | 5,602 | 5,494 |
| 50% Serum (B+) w/ RITUXIMAB | 4,052 | 10,260 | 9,408 | 9,575 |
|  | 4,847 | 11,918 | 12,799 | 10,572 |
| 50% Serum (B+) w/ 1F5 | 9,023 | 9,500 | 8,002 | 9,986 |
|  | 10,281 | 10,393 | 9,106 | 6,999 |
| 50% Serum (B+) w/ RITUXIMAB + mAb 3E7 | 3,230 | 3,763 | 6,685 | 5,370 |
|  | 3,473 | 3,216 | 4,507 | 6,254 |
| 50% Serum (B+) w/ 1F5 + mAb3E7 | 4,893 | 4,581 | 8,501 | 7,081 |
|  | 6,642 | 5,743 | 7,231 | 7,583 |

TABLES 5A-D

Table 5A

| Raji (1 × 10⁵) | 1 Hr G4 Live | 24 Hr G4 Live | 48 Hr G4 Live | 72 Hr G4 Live |
|---|---|---|---|---|
| 50% Serum (A+) | 7,097 | 14,796 | 30,167 | 33,584 |
|  | 6,246 | 13,509 | 25,090 | 38,653 |
| 50% Serum (A+) w/ RITUXIMAB | 3,124 | 2,030 | 3,861 | 3,687 |
|  | 3,221 | 1,669 | 2,054 | 3,329 |
| 50% Serum (A+) w/ 1F5 | 1,646 | 2,446 | 10,484 | 9,167 |
|  | 1,067 | 2,417 | 11,506 | 5,757 |
| 50% Serum (A+) w/ RITUXIMAB + mAb 3E7 | 234 | 212 | 391 | 671 |
|  | 380 | 213 | 341 | 1,420 |
| 50% Serum (A+) w/ 1F5 + mAb3E7 | 28 | 121 | 198 | 999 |
|  | 26 | 99 | 334 | 3,423 |

Table 5B

| Raji (1 × 10⁵) | 1 Hr G4 Total | 24 Hr G4 Total | 48 Hr G4 Total | 72 Hr G4 Total |
|---|---|---|---|---|
| 50% Serum (A+) | 9,476 | 17,856 | 35,143 | 40,494 |
|  | 8,295 | 16,275 | 29,255 | 45,669 |
| 50% Serum (A+) w/ RITUXIMAB | 8,918 | 12,737 | 18,557 | 18,218 |
|  | 8,332 | 11,289 | 12,082 | 16,135 |
| 50% Serum (A+) w/ 1F5 | 9,921 | 10,898 | 20,794 | 18,110 |
|  | 9,717 | 10,696 | 21,634 | 14,075 |
| 50% Serum (A+) w/ RITUXIMAB + mAb 3E7 | 3,967 | 7,102 | 8,866 | 10,045 |
|  | 5,052 | 7,503 | 8,253 | 12,978 |
| 50% Serum (A+) w/ 1F5 + mAb3E7 | 7,495 | 6,062 | 6,162 | 8,277 |
|  | 6,299 | 7,057 | 4,859 | 13,438 |

TABLES 5A-D-continued

Table 5C

| Raji (1 × 10$^5$) | 1 Hr G1 Live | 24 Hr G1 Live | 48 Hr G1 Live | 72 Hr G1 Live |
|---|---|---|---|---|
| 50% Serum (A+) | 6,828 | 13,230 | 17,387 | 10,290 |
|  | 5,977 | 11,848 | 16,161 | 13,339 |
| 50% Serum (A+) w/ RITUXIMAB | 2,856 | 1,864 | 2,973 | 2,685 |
|  | 2,946 | 1,522 | 1,689 | 2,307 |
| 50% Serum (A+) w/ 1F5 | 1,406 | 2,112 | 7,157 | 6,202 |
|  | 856 | 2,088 | 7,937 | 3,895 |
| 50% Serum (A+) w/ RITUXIMAB + mAb 3E7 | 204 | 188 | 323 | 540 |
|  | 348 | 195 | 283 | 1,071 |
| 50% Serum (A+) w/ 1F5 + mAb3E7 | 15 | 97 | 156 | 737 |
|  | 18 | 88 | 275 | 2,499 |

Table 5D

| Raji (1 × 10$^5$) | 1 Hr G4 Dead | 24 Hr G4 Dead | 48 Hr G4 Dead | 72 Hr G4 Dead |
|---|---|---|---|---|
| 50% Serum (A+) | 1,352 | 2,012 | 2,558 | 2,675 |
|  | 1,158 | 1,813 | 2,080 | 2,809 |
| 50% Serum (A+) w/ RITUXIMAB | 4,131 | 10,128 | 12,929 | 13,292 |
|  | 3,690 | 9,091 | 9,519 | 11,660 |
| 50% Serum (A+) w/ 1F5 | 7,449 | 8,196 | 9,386 | 8,294 |
|  | 8,323 | 8,047 | 8,831 | 6,330 |
| 50% Serum (A+) w/ RITUXIMAB + mAb 3E7 | 3,393 | 6,563 | 8,199 | 8,796 |
|  | 4,197 | 6,947 | 7,658 | 10,254 |
| 50% Serum (A+) w/ 1F5 + mAb3E7 | 7,379 | 5,810 | 5,850 | 6,696 |
|  | 6,177 | 6,866 | 4,349 | 8,681 |

In summary, RITUXIMAB was found to effectively kill Raji cells only in the presence of serum. In almost all experiments, 3E7 (an anti-C3b(i) antibody) was observed to enhance the killing capacity of RITUXIMAB. Similar results have been obtained with the mAb 1F5/mAb 3E7 pair. See representative results in Tables 2-5. These results were all part of a single experiment. Three different sera were used, as well as media.

Applicants contend that the most important mechanism of action of RITUXIMAB requires complement activation, and thus CH5O values of the patients' sera will be useful in assessing the effectiveness of RITUXIMAB therapy. In principle the flow cytometric analysis paradigm could be used to screen for the efficacy of RITUXIMAB±3E7 in vitro, based on samples of blood taken from a patient, under conditions which allow for complement activation. If the patient's CH5O is low, or killing is weak, supplementation with fresh plasma from a compatible donor or addition of one or more purified complement components would be indicated.

Example 2

Administration of RITUXIMAB Depletes Available Complement

Quantitative flow cytometry was used to measure RTX-mediated C3b(i)-opsonization of ARH 77 cells (Tables 6A, 6B). In this procedure the cells are reacted with NHS and RTX, and after a wash they are probed with fluorescent labeled mAb 3C11, a mAb that is also specific for C3b(i). In parallel, calibrated fluorescent beads, which have known numbers of fluorescent molecules bound, are also examined by flow cytometry. In this way, by comparison to the bead standards, it is possible to obtain a quantitative readout (MESF, molecules of equivalent soluble fluorochrome) for the RTX-opsonized cells. The results indicate that at higher cell concentrations the ability of serum to facilitate robust C3b(i) opsonization in the presence of RTX decreases. A large excess of RTX was used in these experiments, and so a lack of RTX was not the reason for the decrease. Supplementation of the sera with purified C2, either native, or oxidized (to further enhance C activation) clearly enhanced C3b(i) deposition, and this effect was evident at lower serum concentrations as well.

As previously mentioned, it is likely that the limiting factor in complement activity is C2, and this example shows that both C2 and its more stable oxidized form can enhance or restore C activity, as defined by opsonization.

TABLE 6A

Addition of Complement Component C2 Enhances RITUXIMAB -mediated C3b(i) Opsonization* of ARH77 Cells in Serum

| Condition: | | MESH Units Cell Concentration (cells/ml) | | |
|---|---|---|---|---|
|  |  | 2 × 10$^6$ | 4 × 10$^6$ | 8 × 10$^6$ |
| 50% serum | + RTX | 210,000 | 110,000 | 40,000 |
|  | + RTX + C2 | 290,000 | 150,000 | 100,000 |
| 25% serum | + RTX | 100,000 | 57,000 | 32,000 |
|  | + RTX + C2 | 300,000 | 190,000 | 67,000 |

*Quantitative flow cytometry readout: Al488 anti-C3b(i) mAb 3C11.

TABLE 6B

Addition of Complement Component C2 or Oxidized C2 Enhances RITUXIMAB -mediated C3b(i) Opsonization* of ARH77 Cells in Serum

| Condition: | | MESH Units Cell Concentration (cells/ml) | |
|---|---|---|---|
|  |  | 2 × 10$^6$ | 4 × 10$^6$ |
| 50% serum | + RTX | 360,000 | 240,000 |
|  | + RTX + C2 | 420,000 | 290,000 |
|  | + RTX + Ox-C2 | 510,000 | 335,000 |
| 25% serum | + RTX | 270,000 | 160,000 |
|  | + RTX + C2 | 380,000 | 270,000 |
|  | + RTX + Ox-C2 | 395,000 | 230,000 |

*Quantitative flow cytometry readout: Al488 anti-C3b(i) mAb 3C11. Serum used was different from that used in Table 6A experiment.

Example 3

Supplementation of Patient Blood with Complement Enhances C3b(i) Deposition

Experimental evidence has been generated in support of the paradigm that supplementation with complement can enhance the efficacy of anti-cancer antibodies in killing their target cells. In particular, experiments on whole blood isolated from a patient with a B cell lymphoma were performed and demonstrate that supplemental complement can enhance C3b(i) deposition. The whole blood was collected in citrate to prevent coagulation but the citrated plasma is still permissive for complement activation. RITUXIMAB± an anti-C3b(i) (3E7) mAb was added to the blood, and then flow cytometry and a phycoerythrin (PE)-labeled mAb specific for C3b(i) (7C12, which recognizes an epitope different from that bound by 3E7) was used to measure deposition of C3b(i) on the cancer cells. The amount of C3b(i) deposited on the cancer cells provides a readout of the effectiveness of the RITUX- IMAB to activate complement in the medium (citrated plasma or serum) being tested. The 3E7 mAb was use because it will enhance C3-mediated deposition promoted by RITUX-IMAB. The entire experiment was conducted in a parallel study in which the patient's blood cells were washed several times and then reconstituted in an AB±plasma from a normal healthy blood donor. Control experiments were conducted in blood anti-coagulated with EDTA, because complement activation is completely blocked by EDTA.

The results shown in Table 7 clearly indicate that complement activation in the patient's own plasma is quite modest, as manifested in the weak staining of the cancer cells with the PE-labeled anti-C3b(i) mAb, 7C12. However, when plasma from a healthy normal donor was substituted for patient plasma, a very high level of C3b(i) deposition was demonstrable on the cancer cells. Thus, supplementation of complement by iv infusion of normal compatible donor plasma is clearly indicated for this patient.

TABLE 7

| Plasma | Additions | PE-7C12 staining Log Mean Fluorescence |
|---|---|---|
| Citrated patient | Nothing | <15 |
| | RITUXIMAB | 180 |
| | RITUXIMAB and mAb 3E7 | 215 |
| Citrated normal (AB+) | Nothing | <60 |
| | RITUXIMAB | 1723 |
| | RITUXIMAB and mAb 3E7 | 1821 |
| EDTA patient | Nothing | <15 |
| | RITUXIMAB | <50 |
| | RITUXIMAB and mAb 3E7 | <50 |

The magnitude of the log mean fluorescence is indicative of the degree of C3b(i) opsonization induced by RITUX-IMAB. In EDTA plasma, where complement is blocked, or in the patient's citrated plasma, C3b(i) deposition is quite low. RITUXIMAB was added at 10 ug/ml and mAb 3E7 was added at 3 ug/ml.

Example 4

RTX-Mediated Killing of DB Cells by Complement is Enhanced by Addition of Complement Component C2

Figure 1B:
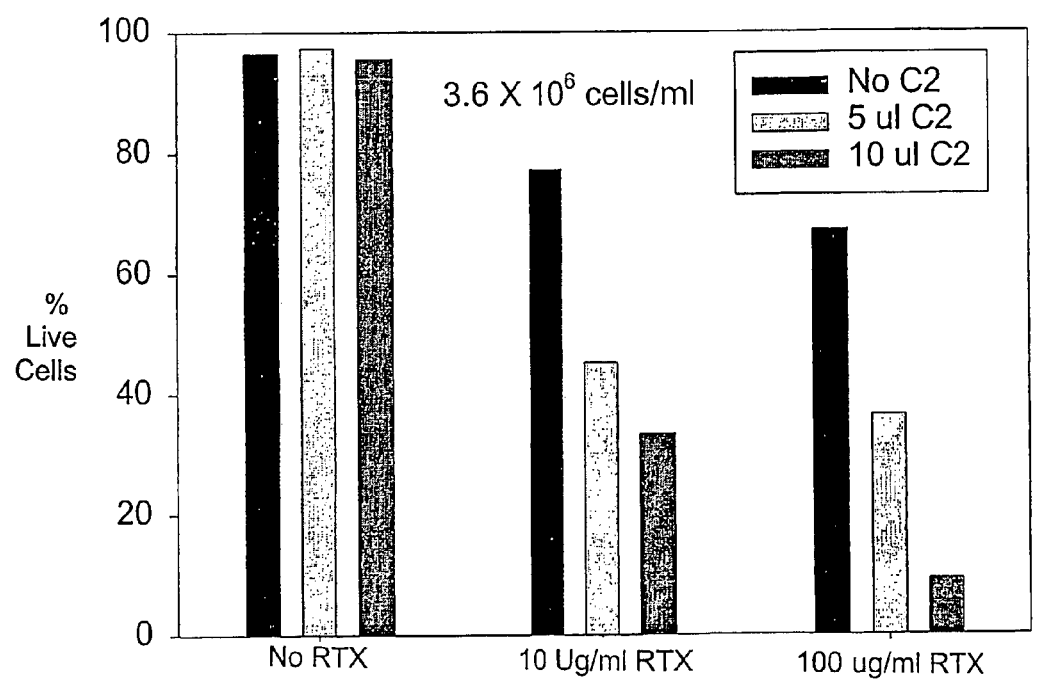

FIGS. 1A and 1B illustrate the results of an experiment in which flow cytometry was used to measure RTX-mediated killing of DB cells over the course of a 24 hour incubation. The general methodology was identical to that previously reported in Tables 2-5 for Raji cells. At the lower cell concentrations RTX-mediated killing is moderately good, especially at a RTX concentration of 100 ug/ml (see FIG. 1A). However, at higher cell concentrations ($3.6 \times 10^6$ cells/ml vs $4.0 \times 10^5$ cells/ml), even the use of 100 ug/ml RTX leaves more than half of the cells alive after 24 hours (see FIG. 1B). It is likely that the limiting factor in this killing assay is the capacity of complement to kill so many cells. In fact, supplementation of the serum with C2 leads to a substantial increase in killing, as illustrated in the large drop in live cells in the presence of both RTX and C2. Note that C2 by itself in' serum does not promote killing. This example provides additional evidence that addition of C2 can enhance killing of cancer cells, even when the complement source is from a normal donor.

Example 5

Binding of RTX to Large Numbers of Cells Depletes Complement, and Addition of C2 can Restore Complement Activity In this experiment RTX (10 or 100 ug/ml) was incubated with target cancer cells in NHS for one hour at 37 degrees C, and then the cells were pelleted and the residual level of complement in the NHS was measured in a CH50 assay. Although there was no drop in complement activity if the cell concentrations were 106 per ml or lower, at higher cell concentrations consumption of complement was clearly evident. In fact, at cell concentrations of $10^8$ per ml, more than 80% of the complement was consumed due to binding of RTX to the cells and formation of complement-fixing immune complexes. There was no loss of complement activity for cells alone or for RTX alone.

The results illustrated in Table 8 indicate that the major reason for the loss of complement activity must have been due to consumption of complement component C2. That is, when C2 is added to the depleted supernatants (SN), in all but one case full complement activity is restored. This study is relevant because in certain hematologic malignancies the burden of tumor cells in the circulation can reach $10^8$ per ml. Alternatively, binding of anti-tumor mAbs to tumor masses in organs, of ~200 ml or more would also be expected to substantially deplete complement. This experiment argues that C2 may be sufficient in many cases to restore complement activity and restore the killing capacity of the anti-tumor mAb.

TABLE 8

Restoration of Complement Activity by Addition of Complement Component C2

| | CH50 | | | |
|---|---|---|---|---|
| SN from 1 hr 37° C. | 10 ug/ml RTX | | 100 ug/ml RTX | |
| incubation with $1 \times 10^8$ cells/ml | No addition | Addition of C2 | No addition | Addition of C2 |
| ARH-77 | 108 | >300 | 57 | 252 |
| Raji | 127 | >300 | 46 | 297 |
| DB | 84 | 266 | 28 | 117 |

Cells + serum + RTX were incubated for 1 hour, resulting in consumption of complement. After the cells were pelleted, the supernatants were tested for complement activity (±C2) in a CH50 assay. Naive serum had a CH50 of ~275 (normal range, 150-300).

Example 6

Treatment of a Chronic Lymphocytic Leukemia Patient with RITUXIMAB Leads to Substantial and Prolonged Depletion of Complement The complement activity of a Chronic Lymphocytic Leukemia (CLL) patient receiving RTX treatment was monitored over the course of the four weeks of treatment. The results illustrated in Table 9 indicate that although the patient had a high level of complement activity before RTX treatment, his complement levels were severely reduced as a consequence of treatment. The assay results are based on a complete multi-point titration (serum/5 to serum/320) for each serum sample, and are normalized to 100 for the initial serum sample (pre-treatment). In this assay, each serum dilution is tested, in duplicate, for its ability to facilitate lysis of antibody-sensitized sheep red blood cells. Selected samples were also tested for CH50 at the UVA clinical lab, which uses a single serum concentration to lyse sensitized sheep red blood cells; this later assay is therefore based in part on extrapolation. The CH50 value for the pre-treatment bleed was 242. The results for the next 8 consecutive bleeds are: 242, 68, 204, 167, 89, 60, 56, 58. Thus, the results obtained by the clinical lab also indicate a profound reduction of complement activity, but some of the single points tend to be higher than those obtained by the more complete multipoint assay. These findings also suggest that more careful and comprehensive analyses of complement activity, rather than a single point clinical determination, will be required to fully assess the complement status of a patient. Such assays would include the complete multipoint assay as well as tests with RTX and cancer cells, as mentioned above.

TABLE 9

Decrease in Complement Activity During the Course of RTX Treatment

|  | Week 1 | Week 2 | Week 3 | Week4 |
|---|---|---|---|---|
| Pre-infusion | 100 | 50 | ≦10 | ≦10 |
| 1 hour | 90 | 30 | <10 | ≦10 |
| Post-infusion | 20 | 30 | <10 | ≦10 |

Each week the CLL patient received 375 mg/m$^2$ of RTX, IV over 6-8 hours. The pre-infusion sample was taken before the start of each infusion. The 1 hour sample was taken after 10-15% of the infusion was complete, and the post-infusion sample was taken soon after the infusion was completed. Values are normalized to 100 for the initial pre-infusion sample.

The invention claimed is:

1. A method of enhancing the cytotoxic activity of chimeric anti-CD20 monoclonal antibody IDEC-C2B8 for its target cells in a patient suffering from a neoplastic disease, said method comprising
   administering to said patient a composition comprising said chimeric anti-CD20 monoclonal antibody; and
   administering to said patient a composition comprising compatible human serum or citrated plasma comprising complement component 2.

2. The method claim 1 wherein the monoclonal antibody IDEC-C2B8 and the human complement factor are combined and administered as a single composition.

3. The method of claim 1 wherein the human serum or plasma is prepared from AB type blood.

4. A method of enhancing the cytotoxic activity of chimeric anti-CD20 monoclonal antibody IDEC-C2B8 (RITUXIMAB) for its target cells in a patient suffering from a neoplastic disease, said method comprising
   measuring the complement levels in a blood sample obtained from said patient; and
   administering said monoclonal antibody IDEC-C2B8 in conjunction with administering a composition comprising compatible human serum or citrated plasma comprising complement component 2 to said patient when the complement levels of said patient are insufficient to support adequate complement activation.

5. The method of claim 4 wherein the patient having insufficient levels of complement is identified by
   contacting a serum or plasma sample obtained from said patient with the monoclonal antibody IDEC-C2B8 to form a reaction mixture;
   incubating the reaction mixture in the presence absence of human serum or plasma complement proteins; and
   determining whether the sample exhibits higher opsonization or cell killing in the presence of human serum or plasma complement as the criteria for identifying a patient having insufficient levels of complement and that would be administered both the monoclonal antibody IDEC-C2B8 and said human serum or plasma.

6. The method of claim 4 wherein the monoclonal antibody IDEC-C2B8 and the human serum or plasma are administered as a single composition.

7. The method of claim 4 wherein said human serum or plasma is administered in conjunction with the monoclonal antibody IDEC-C2B8 when the measured CH50 level of said patient's blood sample is 150 or lower.

* * * * *

UNITED STATES PATENT AND TRADEMARK OFFICE
CERTIFICATE OF CORRECTION

PATENT NO. : 7,858,087 B2  
APPLICATION NO. : 11/881036  
DATED : December 28, 2010  
INVENTOR(S) : Taylor et al.

Page 1 of 1

It is certified that error appears in the above-identified patent and that said Letters Patent is hereby corrected as shown below:

In Claim 2, column 20, line 1, please insert --of-- after "method" and immediately before "claim."

In Claim 5, column 20, line 25, please insert --or-- after "presence" and immediately before "absence."

Signed and Sealed this  
Fifteenth Day of February, 2011

David J. Kappos  
*Director of the United States Patent and Trademark Office*